(12) United States Patent
Keusenkothen et al.

(10) Patent No.: US 9,957,203 B2
(45) Date of Patent: May 1, 2018

(54) PRODUCTION OF AROMATICS FROM METHANOL USING SELECTIVE HYDROGEN COMBUSTION

(71) Applicant: ExxonMobil Chemical Patents Inc., Baytown, TX (US)

(72) Inventors: Paul F. Keusenkothen, Houston, TX (US); Seth M. Washburn, Houston, TX (US); Neeraj Sangar, League City, TX (US); Nikolaos Soultanidis, Houston, TX (US); Mayank Shekhar, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 112 days.

(21) Appl. No.: 14/876,952

(22) Filed: Oct. 7, 2015

(65) Prior Publication Data
US 2016/0145170 A1 May 26, 2016

Related U.S. Application Data

(60) Provisional application No. 62/082,668, filed on Nov. 21, 2014.

(51) Int. Cl.
| | |
|---|---|
| *C07C 1/20* | (2006.01) |
| *B01J 29/82* | (2006.01) |
| *B01J 29/04* | (2006.01) |
| *B01J 8/06* | (2006.01) |
| *B01J 8/18* | (2006.01) |

(Continued)

(52) U.S. Cl.
CPC ............... *C07C 1/20* (2013.01); *B01J 8/0221* (2013.01); *B01J 8/0278* (2013.01); *B01J 8/0285* (2013.01); *B01J 8/06* (2013.01); *B01J 8/1863* (2013.01); *B01J 8/26* (2013.01); *B01J 2208/00309* (2013.01)

(58) Field of Classification Search
CPC ......... C07C 1/20; B01J 8/0285; B01J 8/0278; B01J 8/26; B01J 8/1863; B01J 8/06; B01J 8/0221; B01J 2208/00309
See application file for complete search history.

(56) References Cited

U.S. PATENT DOCUMENTS

| | | |
|---|---|---|
| 3,894,102 A | 7/1975 | Chang et al. |
| 3,894,103 A | 7/1975 | Chang et al. |

(Continued)

FOREIGN PATENT DOCUMENTS

| | | |
|---|---|---|
| CN | 1880288 | 12/2006 |
| WO | 2007/067285 | 6/2007 |
| WO | 2007/123523 | 11/2007 |

OTHER PUBLICATIONS

U.S. Appl. No. 62/057,855, filed Sep. 30, 2014, Vijay et al.

(Continued)

*Primary Examiner* — Brian A McCaig
*Assistant Examiner* — Jason Y Chong

(57) ABSTRACT

A catalyst system and processes for combined aromatization and selective hydrogen combustion of oxygenated hydrocarbons are disclosed. The catalyst system contains at least one aromatization component and at least one selective hydrogen combustion component. The process is such that the yield of hydrogen is less than the yield of hydrogen when contacting the hydrocarbons with the aromatization component alone.

10 Claims, 1 Drawing Sheet

(51) Int. Cl.
*B01J 8/26* (2006.01)
*B01J 8/02* (2006.01)

(56) References Cited

U.S. PATENT DOCUMENTS

| | | | |
|---|---|---|---|
| 3,894,104 A | 7/1975 | Chang et al. | |
| 3,894,107 A | 7/1975 | Butter et al. | |
| 4,035,430 A | 7/1977 | Dwyer et al. | |
| 4,049,573 A | 9/1977 | Kaeding | |
| 4,058,576 A | 11/1977 | Chang et al. | |
| 4,088,706 A | 5/1978 | Kaeding | |
| 5,002,653 A | 3/1991 | Kennedy et al. | |
| 5,059,738 A * | 10/1991 | Beech, Jr. | B01J 29/90 502/34 |
| 5,430,210 A | 7/1995 | Grasselli et al. | |
| 5,527,979 A | 6/1996 | Agaskar et al. | |
| 7,700,816 B2 * | 4/2010 | Xu | B01J 21/063 502/214 |
| 8,350,108 B2 * | 1/2013 | Cortright | B01J 23/6567 585/331 |
| 2004/0152586 A1 | 8/2004 | Ou et al. | |
| 2007/0249740 A1 | 10/2007 | Iaccino et al. | |
| 2011/0040135 A1 | 2/2011 | Iaccino et al. | |
| 2013/0303814 A1 * | 11/2013 | Mammadov | B01J 29/405 585/408 |
| 2015/0065769 A1 | 3/2015 | Henao et al. | |
| 2015/0141703 A1 * | 5/2015 | Dubois | B01J 8/065 568/486 |

OTHER PUBLICATIONS

Grasselli et al., "*Catalytic dehydrogenation (DH) of light paraffins combined with selective hydrogen combustion (SHC),*" Appl. Catal. A, vol. 1, pp. 1-8 (1999).

* cited by examiner

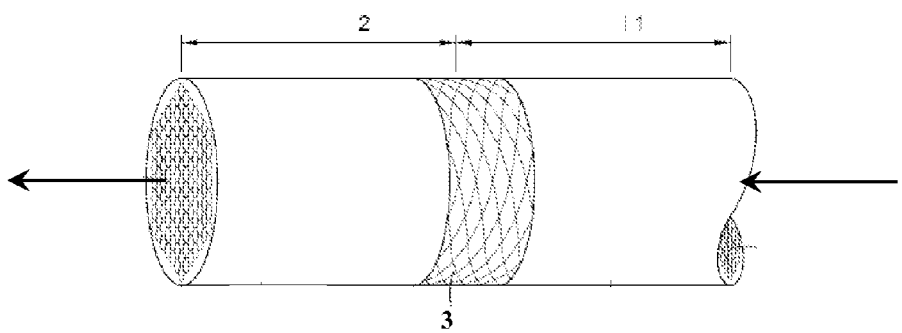

PRODUCTION OF AROMATICS FROM METHANOL USING SELECTIVE HYDROGEN COMBUSTION

CROSS REFERENCE TO RELATED APPLICATIONS

This application claims priority to and the benefit of U.S. Provisional Application Ser. No. 62/082,668 filed Nov. 21, 2014, which is incorporated herein by reference.

FIELD OF THE INVENTION

The present invention relates to a catalyst system and its use in processes involving aromatization of oxygenated hydrocarbons. The catalyst system is particularly useful in reducing the concentration of hydrogen in aromatization products.

BACKGROUND OF THE INVENTION

Conversion of various feeds to aromatic compounds is an industrially valuable process. Some conventional methods can include conversion of methanol and/or olefins to aromatics in the presence of a molecular sieve, such as ZSM-5. Reactions for conversion of methanol and/or olefins to aromatics can be useful, for example, for creation of aromatics as individual products, or for formation of aromatic and olefin mixtures for use as naphtha boiling range or distillate boiling range fuels.

U.S. Pat. Nos. 4,049,573 and 4,088,706 disclose that methanol can be converted to a hydrocarbon mixture rich in $C_2$-$C_3$ olefins and mononuclear aromatics, particularly p-xylene, by contacting the methanol at a temperature of 250-700° C. and a pressure of 0.2 to 30 atmospheres with a crystalline aluminosilicate zeolite catalyst which has a Constraint Index of 1-12 and which has been modified by the addition of an oxide of boron or magnesium either alone or in combination or in further combination with oxide of phosphorus. The above-identified disclosures are incorporated herein by reference.

Methanol can be converted to gasoline employing the MTG (methanol to gasoline) process. The MTG process is disclosed in the patent art, including, for example, U.S. Pat. Nos. 3,894,103; 3,894,104; 3,894,107; 4,035,430 and 4,058,576. U.S. Pat. No. 3,894,102 discloses the conversion of synthesis gas to gasoline. MTG processes provide a simple means of converting syngas to high-quality gasoline. The ZSM-5 catalyst used is highly selective to gasoline under methanol conversion conditions, and is not known to produce distillate range fuels, because the $C_{10}$+ olefin precursors of the desired distillate are rapidly converted via hydrogen transfer to heavy polymethylaromatics and $C_4$ to $C_8$ isoparaffins under methanol conversion conditions.

Chinese Patent No. 1,220,288 describes a methanol conversion to aromatics ("MTA") technology. The MTA technology makes use of modified zeolite catalysts to convert methanol to liquid hydrocarbon products containing aromatics.

Solid oxygen carrier selective hydrogen combustion ("SHC") catalysts are unique materials where oxygen used to oxidize hydrogen is bound up in the lattice of the catalysts. Due to size exclusion, these materials have been found to be very selective to react with hydrogen alone. For example, U.S. Pat. No. 5,430,210 incorporated herein by reference describes contacting a hydrocarbon and hydrogen stream and an oxygen containing stream with separate surfaces of a metal oxide membrane impervious to non-oxygen containing gases. The metal oxide membrane was selective for hydrogen combustion.

Grasselli et al., *Catalytic dehydrogenation (DH) of light paraffins combined with selective hydrogen combustion (SHC)*, Appl. Catal. A 189 (1999) 1, pp. 1-8, described conversion of propane to propylene that was twice the thermodynamic limit with selectivity to propylene in excess of 90% using $Bi_2O_3$ as an SHC catalyst mixed with platinum-based propylene dehydrogenation catalyst. The process operated on intermittent feed cycles of propane and air to regenerate the catalyst. While initial conversion data was promising, the $Bi_2O_3$ catalyst was not stable.

Methanol conversion to aromatics is non-selective and exothermic. Insufficient heat removal can lead to run-away temperature excursions that negatively affect aromatic selectivity. There is an ongoing desire to improve methods of converting methanol to aromatics that yield a higher amount of aromatics and are less prone to temperature excursions than prior art methods.

SUMMARY OF THE INVENTION

The present invention provides methods for improving the yield of aromatics from conversion of oxygenated hydrocarbon feed, for example, methanol. In one aspect, the invention relates to a catalyst system comprising at least one aromatization component and at least one selective hydrogen combustion ("SHC") component. The multi-component catalyst system permits simultaneous conversion of oxygenated hydrocarbon feeds to aromatics and selective combustion of the resulting hydrogen to water. It is believed that selectively combusting the hydrogen produced during conversion of oxygenated hydrocarbon to aromatics shifts the thermodynamic equilibrium in favor of greater aromatic production. Additionally, the combustion of hydrogen in the presence of the SHC component is optionally endothermic, which helps manage the heat generated by the exothermic conversion of the oxygenated hydrocarbon to aromatics.

The SHC component of the catalyst system consists essentially of (a) a metal combination and (b) at least one of oxygen and sulfur. At least one of oxygen and sulfur is chemically bound both within and between the metals. The metal combination of the SHC component is selected as follows: i) at least one metal from group 3 and at least one metal from groups 4-15 of the Periodic Table of the Elements; ii) at least one metal from groups 5-15 of the Periodic Table of the Elements, and at least one metal from at least one of groups 1, 2, and 4 of the Periodic Table of the Elements; iii) at least one metal from groups 1-2, at least one metal from group 3, and at least one metal from groups 4-15 of the Periodic Table of the Elements; and iv) two or more metals from groups 4-15 of the Periodic Table of the Elements.

The aromatization component of the catalyst system comprises at least one molecular sieve, for example, ZSM-5. A further option, the aromatization component additionally comprises a group 8-14 element or a combination of metals from the same group of the Periodic Table.

Another aspect of the invention relates to a hydrocarbon conversion process, comprising several steps. First, provide a flow-through reactor system containing a catalyst system comprising at least one aromatization component and at least one selective hydrogen combustion component. Second, during a first time interval, execute the following sub-steps: i) pass oxidant through the flow-through reactor system, ii) transfer at least a portion of the oxidant's oxygen to the selective hydrogen combustion component for storage, iii) remove at least a portion of any coke from the catalyst system by oxidation or combustion with the oxidant's oxygen, and iv) lessen or discontinue the passing of the oxidant through the flow-through reactor. Third, during a second time interval, execute the following sub-steps: i) pass an oxygenated hydrocarbon feed through the flow-through reactor system, ii) convert at least a portion of the oxygenated hydrocarbon feed to aromatics and hydrogen in the presence of at least the aromatization component of the catalyst system, and iii) selectively combust at least a portion of the hydrogen with stored oxygen in the selective hydrogen combustion component of the catalyst system to form water without substantially combusting any of the aromatics or any of the oxygenated hydrocarbon feed. Finally, conduct at least a portion of a conversion products mixture comprising aromatics and water away from the flow-through reactor system.

Yet another aspect of the invention relates to a hydrocarbon conversion process comprising several steps. First, charge at least one oxygenated hydrocarbon feed to a fluidized bed reactor. Second, charge a fluidized catalyst system from a catalyst regenerator to the fluidized bed reactor. The catalyst system comprises at least one aromatization component and at least one selective hydrogen combustion component. Third, catalytically convert the oxygenated hydrocarbon feed to aromatics and combust resultant hydrogen. Perform the conversion to aromatics and the hydrogen combustion in the presence of the catalyst system to produce conversion products comprising aromatics and water, and an at least partially deactivated catalyst system. Discharge the products and spent catalyst system from the reactor. Fourth, separate a phase rich in the conversion products from a phase rich in the deactivated catalyst system. Fifth, strip any retained volatile conversion products off the deactivated catalyst system with a stripping material at stripping conditions to produce a stripped catalyst system phase. Sixth, reactivate the stripped catalyst phase with oxidant in the catalyst regenerator at regeneration conditions to produce the fluidized catalyst system. Recycle the fluidized catalyst system to the reactor. Finally, separate and recover the conversion products.

BRIEF DESCRIPTION OF THE DRAWINGS

FIG. 1 schematically illustrates a flow-through reactor.

DETAILED DESCRIPTION OF THE PRESENT INVENTION

For the purpose of this description and appended claims, the following terms are defined:

Unless otherwise stated, all percentages, parts, ratios, and the like are by weight.

Unless otherwise stated, a reference to an element, metal, compound, or component includes the element, metal, compound, or component by itself, as well as in combination with other elements, metal, compounds, or components, such as mixtures of compounds.

Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

Unless otherwise stated, certain terms used herein shall have the following meaning.

The term "olefins" shall mean non-aromatic hydrocarbons having one or more carbon-carbon double bonds. The term "aromatics" shall mean compounds having one or more than one benzene ring. The term "unsaturate" means a hydrocarbon containing at least one carbon atom directly bound to another carbon atom by a double or triple bond.

The term "physical admixture" shall mean a combination of two or more components obtained by mechanical (i.e., non-chemical) means. The term "chemically bound" shall mean bound via atom to atom bonds.

The term "selective hydrogen combustion" shall mean reacting hydrogen with oxygen to form water or steam without substantially reacting hydrocarbons with oxygen to form carbon monoxide, carbon dioxide, and/or oxygenated hydrocarbons. The term "selective hydrogen combustion catalyst" or "selective hydrogen combustion component (when the latter phrase is used to identify one component of a catalyst system) shall broadly mean a material or materials capable of promoting or participating in a selective hydrogen combustion reaction, using either free oxygen or lattice oxygen contained in the selective hydrogen combustion catalyst.

The term "group 3 metals" shall mean elements having atomic numbers of 21, 39, 57 through 71, and 89 through 92.

The term "yield" shall mean weight of a product produced per unit weight of feed, expressed in terms of weight %.

The term "Periodic Table" or "Periodic Table of the Elements" means the Periodic Chart of the Elements, as it appears on the inside cover of The Merck Index, Twelfth Edition, Merck & Co., Inc., 1996.

The term "aromatization" means any process involving both dehydrogenation and cyclization of non-cyclic hydrocarbon, including oxygenated hydrocarbon to produce a hydrocarbon having at least one cyclic structure. The cyclic structures can be saturated or unsaturated and include at least some aromatic structures. The term "aromatization catalyst" and "aromatization component" (when the latter phrase is used to identify one component of a catalyst system) shall mean a material or materials capable of promoting or participating in an aromatization reaction.

The term "residence time" means the average time duration for non-reacting molecules (such as He, N2, Ar) having a molecular weight in the range of 4 to 40 to traverse the reactor or a defined zone within the reactor.

The term "flow-through reactor" refers to a reactor design in which feeds and/or reaction mixtures can flow through the reactor, e.g., where oxidant feeds, oxygenated hydrocarbon feeds, and/or reaction mixtures come into contact with a catalyst system as the feeds and/or reaction mixtures flow through the reactor.

With respect to flow-through reactors, the term "region" means a location within the reactor, e.g., a specific volume within the reactor and/or a specific volume between a flow-through reactor and a second reactor, such as a second flow-through reactor. With respect to flow-through reactors, the term "zone", refers to a specific function being carried out at a location within the flow-through reactor. For example, a "reaction zone" or "reactor zone" is a volume within the reactor for conducting at least one of aromatization and selective hydrogen combustion or oxidation.

The term "tubular reactor" means an elongated, reactor vessel of substantially any cross-section, the vessel being configured to allow fluid flow into, through, and out of the vessel, via first and second apertures, the first and second apertures being located proximate to opposed ends of the elongated reactor vessel.

The term "fixed-bed catalytic reactor" means a reactor having at least one bed of catalyst, wherein the catalyst is substantially retained within the bed.

The present invention provides methods for improving the yield of aromatics from conversion of oxygenated hydrocarbon feed, for example, methanol. The oxygenated hydrocarbon feed can comprise aliphatic aldehydes, carboxylic acids, carbohydrates, alcohols, ethers, acetals and analogs. Preferably, the oxygenated hydrocarbon feed comprises any monohydric alcohol having from 1 to 4 carbon atoms or ethers derived from these alcohols. Thus, methanol, ethanol, n-propanol, isopropanol, n-butanol, sec-butanol and isobutanol may be used either alone or in admixture with ethers derived from such alcohols. Likewise, the noted ethers, e.g., methyl-ethyl ether may be similarly used. Particularly preferred feeds are methanol, dimethyl ether and mixtures thereof. Optionally, the oxygenated hydrocarbon feed also contains $C_1$-$C_5$ alkanes, such as methane and/or propane, for conversion of at least a portion of the alkanes and the majority of oxygenated hydrocarbon to aromatics.

The present invention also relates to a catalyst system and its use in processes involving aromatization of oxygenated hydrocarbons. The catalyst system of the present invention comprises (1) at least one aromatization component and (2) at least one hydrogen removal component. The catalyst system of the present invention is multifunctional in that the aromatization component converts oxygenated hydrocarbon to aromatics and hydrogen (among other products) and the hydrogen removal component removes or consumes hydrogen produced from the aromatization reactions. Removal of hydrogen improves selectivity to aromatics by shifting equilibria in favor of unsaturated products.

Suitable hydrogen removal component of the catalyst system may be selective hydrogen combustion ("SHC") catalyst. Selective hydrogen combustion is conversion of hydrogen to water via oxidation or combustion without substantially reacting hydrocarbons with oxygen to form carbon monoxide, carbon dioxide, and/or oxygenated hydrocarbons. In other words, less than 10 wt. %, preferably less than 5 wt. %, of hydrocarbons react with oxygen to form carbon monoxide, carbon dioxide, and/or oxygenated hydrocarbons. The hydrogen removal component is not limited to SHC catalyst for removal of hydrogen. Other suitable hydrogen removal components include reverse water gas shift ("RWGS") catalyst to convert hydrogen and carbon dioxide to carbon monoxide and water. Still other suitable hydrogen removal components include methanation catalyst to convert hydrogen and carbon monoxide to methane.

The conversion of oxygenated hydrocarbon to aromatics according to the invention involves aromatization reactions, with the main aromatization reactions being carried out in a reaction zone section of at least one reactor. When the oxygenated hydrocarbon feed to the reactor comprises methanol, the aromatization reactions includes the following endothermic reactions:

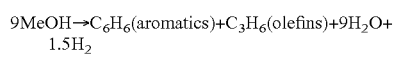

Conversion of methanol to aromatics is exothermic and non-selective. Methane, alkanes, and other non-aromatic naphtha will be produced via undesired side reactions besides the aromatics, olefins, and hydrogen. Additionally, some decomposition of the oxygenated hydrocarbon may occur to form CO and $CO_2$.

The multifunctional catalyst system permits simultaneous conversion of oxygenated hydrocarbon feeds to aromatics and selective combustion of the resulting hydrogen to water. Without being bound by any theory, it is believed the kinetics of hydrogen combustion are much faster than aromatization kinetics. It is believed this kinetic rate difference permits the catalyst system of the present invention to perform aromatization without a substantial co-production of hydrogen. It is further believed that removal of the hydrogen produced by the aromatization reaction (via combustion) would enable oxygenated hydrocarbon conversion having increased aromatic selectivity.

Typically, the products from aromatization of oxygenated hydrocarbons include hydrogen and other less desired side products. Hydrogen usually is not a desirable product due to the difficulty of separation. In addition, due to its low molecular weight, the presence of even a moderate quantity of $H_2$ in the products would consume a significant fraction of a gas compressor's and any other separation equipment volumetric capacities. Converting the hydrogen product into water, which can be easily condensed and separated via any conventional vapor-liquid, liquid-liquid, or other separation device, therefore, debottlenecks the compressors and/or the separation equipment by freeing up the space that would be occupied by the hydrogen. Such newly created space could be used to increase the production of more desirable products such aromatics. Alternatively, at a constant production level, converting hydrogen to water can reduce the number or the size of equipment, thereby reducing the investment costs.

In accordance with the present invention, a catalyst system comprises an aromatization component and a selective hydrogen combustion component, which catalyst system, upon contact with an oxygenated hydrocarbon feed, simultaneously aromatizes the oxygenated hydrocarbon and selectively combusts the hydrogen produced from the aromatizing reaction.

Preferably, the yield of hydrogen is less than the yield of hydrogen when contacting said oxygenated hydrocarbon feed(s) with said aromatization component alone under similar reaction conditions. Preferably, the yield of hydrogen is at least 10% less than the yield of hydrogen when contacting said hydrocarbon feed(s) with said aromatization component alone under similar reaction conditions. More preferably, the yield of hydrogen is at least 25% less, more preferably at 50% less, even more preferably at least 75% less than the yield of hydrogen when contacting said oxygenated hydrocarbon feed(s) with said aromatization component alone under similar reaction conditions.

Selective hydrogen combustion could also help manage the heat produced by the aromatization of oxygenated hydrocarbon. Although the combustion of hydrogen is exothermic, the overall enthalpy for the reactions involving the SHC component can be net endothermic. For example, the removal of internal lattice oxygen required for the oxidation of hydrogen is endothermic. The heat consumed by the removal of internal lattice oxygen can be greater than the heat released by the combustion of that oxygen with hydrogen. Therefore, a net endothermic SHC component would be an ideal heat sink to manage the heat produced by the exothermic aromatization of oxygenated hydrocarbon feed.

This could reduce the amount of heat removal required to prevent run-away temperature excursions. In some aspects, the SHC component reactions can be sufficiently endothermic that the combined aromatization component and SHC component reactions are net endothermic.

Thus, in accordance with the present invention, a hydrocarbon conversion process comprises contacting an oxygenated hydrocarbon feed with a catalyst system comprising at least one aromatization component and at least one net endothermic selective hydrogen combustion component under suitable conditions to produce aromatics, water, and other products, wherein the conversion process is conducted with a reduction of removed heat than would be required for the conversion process using a catalyst system without at least one net endothermic SHC component. Removed heat can be reduced by at least 2%, preferably by over 5%, 10%, 25%, 50%, 75%, or even more preferably by over 100% by using the catalyst system of the present invention over catalyst systems without at least one net endothermic SHC component. Optionally, the SHC component reactions are sufficiently endothermic that addition of heat is required to maintain process conditions suitable to produce aromatics. Since aromatization reactions are exothermic, the required heat removal or input is simply the overall enthalpy of the reaction. Thus, it is within the skill of one of ordinary skill in the art to calculate the required heat removal or addition based on the enthalpy of the SHC component reactions.

The selective hydrogen combustion can be conducted with the feeding of free-oxygen containing gas or by using SHC materials that contain bound or lattice oxygen. It is preferred that selective hydrogen combustion is conducted via the use of lattice oxygen stored in and released from the selective hydrogen combustion component to promote selective hydrogen combustion.

In accordance with the present invention, lattice oxygen in the SHC component of the catalyst system is used as the source of oxygen for the selective hydrogen combustion reaction. Higher hydrogen combustion selectivity and less $CO_x$ by-product are achievable using this approach as compared to co-feeding oxygen to the reactor.

While using lattice oxygen in the SHC component for hydrogen combustion is advantageous, it also has a potential problem. Over time, the lattice oxygen is consumed with a resultant loss of SHC component catalyst activity. However, the SHC component activity may be recovered by regenerating the catalyst with fresh oxidant.

When lattice oxygen in the SHC component is used as the source of oxygen for combustion, a free-oxygen containing gas ("oxidant") can be used to periodically regenerate or replenish the SHC component. Typically, the oxidant includes one or more of molecular oxygen ($O_2$), $O_2^-$, $O_2^=$, ionized oxygen atoms, nitrogen oxides such as $N_2O$, etc. Oxidant is typically in the vapor phase at hydrocarbon conversion conditions, but this is not required, and in certain aspects liquid and/or solid oxidant can be used. The oxidant can comprise molecular $O_2$, e.g., ≥90% $O_2$ (molar basis, per mole of oxidant), such as, ≥99%. For example, the oxidant can comprise $O_2$ in air, or $O_2$ obtained or derived from air, e.g., by separation. The oxidant can comprise (or consist essentially of, or consist of) $O_2$ in air. When the oxidant comprises $O_2$ in air, the total feed generally comprises at least a portion of the air's molecular nitrogen as diluent. In other words, when the oxidant comprises molecular oxygen in air, other gasses in the air, such as molecular nitrogen, are considered to be diluent, and are not considered to be part of the oxidant.

Catalyst System

One aspect of the present invention pertains to a catalyst system that comprises (1) at least one aromatization component and (2) at least one selective hydrogen combustion ("SHC") component.

The aromatization component can be in physical admixture with, or chemically bound to, the SHC component. The metals selected from combinations (i), (ii), (iii), or (iv) can be chemically bound, both between and within the groups specified. For example, within combination (ii), it would be within the scope of the present invention for two or more metals from groups 1 and 2 to be chemically bound to each other as well as chemically bound to the metal(s) from groups 5-15. Alternatively, the chemical binding can be only between metals of different groups and not between metals within the same group, i.e., two or more metals from groups 1 and 2 being in admixture with each other but chemically bound to the metal(s) from groups 5-15.

Aromatization Component

Suitable aromatization components are described in U.S. patent application Ser. No. 14/829,399, which is incorporated by reference in its entirety. Aromatization components suitable for use in the inventive catalyst system are a composition of matter comprising a molecular sieve, such as ZSM-5. Optionally, the composition of matter can include a group 8-14 element, or combination of metals from the same group of the Periodic Table. The composition of matter can optionally further comprise phosphorus and/or lanthanum and/or other elements from groups 1-2 and/or groups 13-16 of the Periodic Table that provide structural stabilization. In this sense, the term "comprising" can also mean that the aromatization component can comprise the physical or chemical reaction product of the molecular sieve and the groups 8-14 element or combination of elements from the same group (and optionally phosphorus and/or lanthanum and/or other elements from groups 1-2 and/or groups 13-16). In various aspects, the molecular sieve comprises ≥10.0 wt. % of the aromatization component, or ≥50.0 wt. %, or ≥90.0 wt. %, or ≥95.0 wt. %, or ≥99.0 wt. %.

As used herein the term "molecular sieve" refers to crystalline or non-crystalline materials having a porous structure. Microporous molecular sieves typically have pores having a diameter of ≤ about 2.0 nm. Mesoporous molecular sieves typically have pores with diameters of about 2 to about 50 nm. Macroporous molecular sieves have pore diameters of >50.0 nm.

Additionally or alternatively, some molecular sieves useful herein are described by a Constraint Index of about 1 to about 12. Constraint Index is determined as described in U.S. Pat. No. 4,016,218, incorporated herein by reference for details of the method.

Particular molecular sieves are zeolitic materials. Zeolitic materials are crystalline or para-crystalline materials. Some zeolites are aluminosilicates comprising [SiO4] and [AlO4] units. Other zeolites are aluminophosphates (AlPO) having structures comprising [AlO4] and [PO4] units. Still other zeolites are silicoaluminophosphates (SAPO) comprising [SiO4], [AlO4], and [PO4] units.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof, Additionally or alternatively, the molecular sieves useful herein may be characterized by a ratio of Si to Al. In particular embodiments, the molecular sieves suitable herein include those having a Si/Al ratio of about 0.05 to 0.5, e.g., 0.05 to 0.45, 0.05 to 0.40, 0.05 to 0.35, 0.05 to 0.30, 0.05 to 0.25, 0.05 to 0.20, 0.05 to 0.15, 0.05 to 0.10, 0.10 to 0.50, 0.1 to 0.45, 0.10 to 0.40, 0.10 to 0.35, 0.10 to 0.30, 0.10 to 0.25, 0.10 to 0.20, 0.10 to 0.15, 0.20 to 0.50, 0.2 to 0.45, 0.20 to 0.40, 0.20 to 0.35, 0.20 to 0.30, or 0.20 to 0.25.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference.

Particular molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-34 (U.S. Pat. No. 4,079,095); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein. Other useful molecular sieves include MCM-22, PSH-3, SSZ-25, MCM-36, MCM-49 or MCM-56, with MCM-22. Still other molecular sieves include Zeolite T, ZKS, erionite, and chabazite.

Another option for characterizing a zeolite (or other molecular sieve) is based on the nature of the ring channels in the zeolite. The ring channels in a zeolite can be defined based on the number of atoms included in the ring structure that forms the channel. In some aspects, a zeolite can include at least one ring channel based on a 10-member ring. In such aspects, the zeolite preferably does not have any ring channels based on a ring larger than a 10-member ring. Examples of suitable framework structures having a 10-member ring channel but not having a larger size ring channel include EUO, FER, IMF, LAU, MEL, MFI, MFS, MTT, MWW, NES, SFG, STF, STI, TON, TUN, MRE, and PON.

In some aspects, the aromatization component can also optionally include at least one metal selected from groups 8-14 of the Periodic Table, such as at least two metals (i.e., bimetallic) or at least three metals (i.e., trimetallic). Typically, the total weight of the groups 8-14 elements is ≥0.1 wt. % based on the total weight of the aromatization component. Typically, the total weight of the groups 8-14 element is ≤ about 10.0 wt. %, based on the total weight of the aromatization component. Thus, the range of the amount of the groups 8-14 elements added to the molecular sieve may be 0.1-10.0 wt. %, or 0.1-5.0 wt. %, or 0.1-2.0 wt. %, or 0.5-2.0 wt. %. Of course, the total weight of the groups 8-14 elements shall not include amounts attributable to the molecular sieve itself.

Additionally or alternatively, in some aspects, the aromatization component can also include at least one of phosphorous and/or lanthanum and/or other elements from groups 1-2 and/or group 13-16, such as at least two such elements or at least three such elements. Typically, the total weight of the phosphorous and/or lanthanum and/or other elements from groups 1-2 and/or groups 13-16 is ≥0.1 wt. % based on the total weight of the aromatization component. Typically, the total weight of the phosphorous and/or lanthanum and/or other elements from groups 1-2 and/or groups 13-16 is ≤ about 10.0 wt. %, based on the total weight of the aromatization component. Of course, the total weight of the phosphorous and/or lanthanum and/or other elements from groups 1-2 and/or groups 13-16 shall not include amounts attributable to the molecular sieve itself.

For the purposes of this description and claims, the numbering scheme for the Periodic Table groups corresponds to the current IUPAC numbering scheme. Therefore, a "group 4 metal" is an element from group 4 of the Periodic Table, e.g., Hf, Ti, or Zr. The more preferred molecular sieves are SAPO molecular sieves, and metal-substituted SAPO molecular sieves. In particular embodiments, one or more group 1 elements (e.g., Li, Na, K, Rb, Cs, Fr) and/or group 2 elements (e.g., Be, Mg, Ca, Sr, Ba, and Ra) and/or phosphorous and/or lanthanum may be used. One or more group 7-9 element (e.g., Mn, Tc, Re, Fe, Ru, Os, Co, Rh, and Ir) may also be used. Group 10 elements (Ni, Pd, and Pt) are less commonly used in applications for forming olefins and aromatics, as the combination of a group 10 element in the presence of hydrogen can tend to result in saturation of aromatics and/or olefins. In some embodiments, one or more group 11 and/or group 12 elements (e.g., Cu, Ag, Au, Zn, and Cd) may be used. In still other embodiments, one or more group 13 elements (B, Al, Ga, In, and Tl) and/or group 14 elements (Si, Ge, Sn, Pb) may be used. In a preferred embodiment, the metal is selected from the group consisting of Zn, Ga, Cd, Ag, Cu, P, La, or combinations thereof. In another preferred embodiment, the metal is Zn, Ga, Ag, or a combination thereof.

Particular molecular sieves and groups 2-13-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (E1APSO where E1 is Be, B, Cr, Co, Ga, Fe, Mg, Mn, Ti, or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO), EP-A-0 161 489 (CoAPSO), EP-A-0 158 976 (ELAPO, where EL is Co, Fe, Mg, Mn, Ti, or Zn), U.S. Pat. No. 4,310,440 (AlPO4), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326, and 5,478,787 (MgAPSO), U.S. Pat. No. 4,554,143 (FeAPO), U.S. Pat. Nos. 4,686,092, 4,846,956, and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617, and 4,880,520 (TiAPSO), U.S. Pat. Nos. 4,500,651, 4,551,236, and 4,605,492 (TiAPO), U.S. Pat. No. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066, and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference. In some aspects, the molecular sieve as modified by the group 8-14 element and/or a group 1-2, group 13-16, lanthanum, and/or phosphorous is a ZSM-5 based molecular sieve.

Various methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), International Patent Application WO 01/36329 published May 25, 2001 (surfactant synthesis), International Patent Application WO 01/25151 published Apr. 12, 2001 (staged acid addition), International Patent Application WO 01/60746 published Aug. 23, 2001 (silicon oil), U.S. Patent Application Publication No. 2002-0055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 2002-0115897 published Aug. 22, 2002 (freeze drying the molecular sieve), which are all herein incorporated by reference in their entirety.

SHC Component

Suitable selective hydrogen combustion components are described in U.S. Patent Application Publication No. 2004-0152586 which is incorporated by reference in its entirety. The selective hydrogen combustion ("SHC") component consists of (a) at least one of oxygen and sulfur and (b) a metal combination selected from the group consisting of:
   i) at least one metal from group 3 and at least one metal from groups 4-15 of the Periodic Table of the Elements;
   ii) at least one metal from groups 5-15 of the Periodic Table of the Elements, and at least one metal from at least one of groups 1, 2, and 4 of the Periodic Table of the Elements;
   iii) at least one metal from groups 1 and 2, at least one metal from group 3, and at least one metal from groups 4-15 of the Periodic Table of the Elements; and
   iv) two or more metals from groups 4-15 of the Periodic Table of the Elements,
wherein the at least one of oxygen and sulfur is chemically bound both within and between the metals. It is intended that reference to a metal from each of the noted groups would include mixtures of metals from the respective groups. For example, reference to one or more metals from groups 4-15 includes a mixture of chemically bound metals from groups 4 and 15 of the Periodic Table.

While it is intended that the SHC component consist essentially of the metals from the combination (sub-group) selected along with oxygen and/or sulfur, it is recognized that impurities may be present in the manufacturing process and that impurities from the oxygenated hydrocarbon feed may be adsorbed or incorporated into the crystalline structure of the SHC component. To the extent that such impurities do not render the SHC component ineffective for selective hydrogen combustion, the impurities shall be deemed to be within the scope of this invention.

For the purposes of description of the SHC component of this invention, metals shall be deemed to include all elements classified as alkali metals, alkaline earth metals, transition metals, other metals, and metalloids, excluding hydrogen from group 1; boron from group 13; carbon and silicon from group 14; and nitrogen, phosphorus, and arsenic from group 15.

The preferred metals from groups 1 and 2 are any of lithium, sodium, potassium, rubidium, cesium, beryllium, magnesium, calcium, strontium, and barium.

It is noted that rare earth elements are to be included as group 3 metals. Preferably, the metal(s) from group 3 are any of scandium, yttrium, lanthanum, cerium, praseodymium, neodymium, samarium, europium, gadolinium, terbium, dysprosium, holmium, erbium, thulium, ytterbium, and lutetium.

The metal(s) or element(s) from groups 4-15 can be any metal element or a mixture of metal elements from groups 4-15 of the Periodic Table of the Elements. Preferably, the metal(s) from groups 4-15 is (are) at least one of titanium, vanadium, chromium, manganese, iron, cobalt, nickel, copper, zinc, aluminum, gallium, germanium, zirconium, niobium, molybdenum, ruthenium, rhodium, palladium, silver, indium, tin, antimony, hafnium, tantalum, tungsten, rhenium, iridium, platinum, gold, lead, and bismuth. More preferably, the metal(s) from groups 4-15 is (are) at least one of titanium, manganese, iron, cobalt, nickel, copper, zinc, aluminum, gallium, germanium, zirconium, ruthenium, rhodium, palladium, silver, indium, tin, antimony, hafnium, rhenium, iridium, platinum, gold, and bismuth.

In one embodiment of the present invention, the SHC component is a combination of oxygen and/or sulfur with one or more metals from group 3 and one or more metals from groups 4-15 of the Periodic Table of the Elements (hereinafter "sub-group 1"). Within sub-group 1, the preferred metals from group 3 are at least one of scandium, yttrium, lanthanum, cerium, samarium, ytterbium and praseodymium; and the preferred metals from groups 4-15 are titanium, zirconium, niobium, molybdenum, tungsten, manganese, iron, cobalt, iridium, nickel, palladium, platinum, copper, zinc, aluminum gallium, indium, germanium, tin, antimony, and bismuth. Even more preferred metal(s) from group 3 are at least one of scandium, yttrium, lanthanum, and praseodymium; and more preferred metals from groups 4-15 are one or more of titanium, zirconium, manganese, iron, cobalt, nickel, copper, zinc, aluminum, indium, and tin.

Examples of combinations falling within sub-group 1 of the metal combinations are $Y_aIn_bZn_cMn_dO_{x\pm\delta}$, $La_aMn_bNi_cAl_dO_{x\pm\delta}$, $La_aMn_bAl_cO_{x\pm\delta}$, $Sc_aCu_{b1}Mn_cO_{x\pm\delta}$, $Sc_aZn_bMn_cO_{x\pm\delta}$, $La_aZr_bO_{x\pm\delta}$, $Mn_aSc_bO_{x\pm\delta}$, and $Pr_aIn_bZn_cO_{x\pm\delta}$, where a, b, c, and d are each between 0 and 1, the sum of a through d equals 1 to 3, x is the sum of a through d plus 1, and δ is the vacancy concentration or excess oxygen concentration. While oxygen is indicated in the formulae above, it will be recognized that the positions held by oxygen could be substituted with sulfur.

In an alternative embodiment of the present invention, the SHC component is a combination of oxygen and/or sulfur with one or more metals from groups 5-15 of the Periodic Table of the Elements and one or more metals from at least one of groups 1, 2, and/or group 4 of the Periodic Table of the Elements (hereinafter "sub-group 2"). Within sub-group 2, the preferred metals from groups 5-15 are at least one of niobium, molybdenum, tungsten, manganese, iron, cobalt, iridium, nickel, palladium, platinum, copper, zinc, aluminum gallium, indium, germanium, tin, antimony, and bismuth; the preferred metals from groups 1 and 2 are sodium, potassium magnesium, calcium, strontium, and barium; and the preferred metals from group 4 are titanium and zirconium. Even more preferred metals from Groups 5-15 are, manganese, iron, cobalt, nickel, zinc, aluminum, indium, tin, antimony and bismuth.

Examples of combinations falling within sub-group 2 of the metal combinations are $K_aBa_bMn_cO_{x\pm\delta}$, $K_aMg_b$ $Mn_cO_{x\pm\delta}$, $Na_aMg_bMn_cO_{x\pm\delta}$, $Mn_aMg_bO_{x\pm\delta}$, $K_aSr_bMn_cO_{x\pm\delta}$, $In_aCa_bMn_cO_{x\pm\delta}$, $Bi_aCa_bMn_cCo_dO_{x\pm\delta}$, $Bi_aCa_bMn_cNi_dO_{x\pm\delta}$, $Ca_aMn_bSn_cCo_dO_{x\pm\delta}$, $In_aMg_bMn_cAl_dO_{x\pm\delta}$, $In_aZn_bMn_cAl_dO_{x\pm\delta}$, $Na_aBa_bMn_cO_{x\pm\delta}$, $Na_aCo_bMn_cO_{x\pm\delta}$, $Ca_aMn_bSb_cO_{x\pm\delta}$, $Ca_aMn_bCo_cAl_dO_{x\pm\delta}$, $Sr_aSb_bSn_cMg_dO_{x\pm\delta}$, $K_aCo_bMn_cO_{x\pm\delta}$, $Mn_aMg_bO_{x\pm\delta}$, $Ni_aMg_bMn_cO_{x\pm\delta}$, $Mn_aMg_bAl_cO_{x\pm\delta}$, $Mn_aMg_bTi_cO_{x\pm\delta}$, $Sr_aSb_bCa_cO_{x\pm\delta}$, $Sr_aTi_bSn_cAl_dO_{x\pm\delta}$, $Sr_aMn_bTi_cAl_dO_{x\pm\delta}$, $Ca_aMn_bO_{x\pm\delta}$, $Ca_aZr_bAl_cO_{x\pm\delta}$, $Bi_aCa_bMn_cO_{x\pm\delta}$, $Bi_aSr_bCo_cFe_dO_{x\pm\delta}$, $Ba_aMn_bO_{x\pm\delta}$, $Ca_aMn_bAl_cO_{x\pm\delta}$, $Ca_aNa_bSn_cO_{x\pm\delta}$, and $Ba_aZr_bO_{x\pm\delta}$, where a, b, c, and d are each between 0 and 1, the sum of a through d equals 1 to 3, x is the sum of a through d plus 1, and 6 is the vacancy concentration or excess oxygen concentration. While oxygen is indicated in the formulae above, it will be recognized that the positions held by oxygen could be substituted with sulfur.

In another alternative embodiment of the present invention, the SHC component is a combination of oxygen and/or sulfur with one or more metals from groups 1 and 2, one or more metals from group 3, and one or more metals from groups 4-15 of the Periodic Table of the Elements (hereinafter "sub-group 3"). Within sub-group 3, the preferred metals from groups 1 and 2 are at least one of sodium, potassium, magnesium, calcium, strontium and barium; the preferred metals from group 3 are at least one of scandium, yttrium, lanthanum, cerium, samarium, ytterbium and praseodymium; and the preferred metals from groups 4-15 are at least one of titanium, zirconium, niobium, molybdenum, tungsten, manganese, iron, cobalt, iridium, nickel, palladium, platinum, copper, zinc, aluminum gallium, indium, germanium, tin, antimony, and bismuth. Even more preferred metals from groups 1 and 2 are sodium, potassium, calcium, strontium and barium; from group 3 are scandium, yttrium, and lanthanum; and from groups 4-15 are titanium, manganese, iron, cobalt, nickel, copper, aluminum, gallium, tin and bismuth.

Examples of combinations falling within sub-group 3 of the metal combinations are $La_aCa_bMn_cCo_dTi_eO_{x\pm\delta}$, $La_aCa_bCo_cO_{x\pm\delta}$, $La_aCa_bMn_cNi_dO_{x\pm\delta}$, $La_aCa_bMn_cCo_dSn_eO_{x\pm\delta}$, $La_aCa_bMn_cCo_dAl_eO_{x\pm\delta}$, $La_aCa_bMn_cCo_dO_{x\pm\delta}$, $Ba_aK_bBi_cLa_dO_{x\pm\delta}$, $La_aCa_bMn_cTi_dAl_eO_{x\pm\delta}$, $La_aCa_bCo_cNi_dAl_eO_{x\pm\delta}$, $La_aCa_bCo_cTi_dO_{x\pm\delta}$, $La_aCa_bMn_cO_{x\pm\delta}$, $Ba_aBi_bLa_cO_{x\pm\delta}$, $La_aCa_bMn_cMg_dO_{x\pm\delta}$, $La_aCa_bMn_cFe_dO_{x\pm\delta}$, $La_aSr_bCo_cAl_dO_{x\pm\delta}$, $Ba_aBi_bYb_cO_{x\pm\delta}$, $La_aCa_bMn_cGa_dO_{x\pm\delta}$, $La_aCa_bMn_cSn_dAl_eO_{x\pm\delta}$, $La_aCa_bMn_cCu_dO_{x\pm\delta}$, $La_aCa_bMn_cCo_dGa_eO_{x\pm\delta}$, $La_aCa_bMn_cAl_dO_{x\pm\delta}$, $La_aCa_bCo_cAl_dO_{x\pm\delta}$, $Ba_aBi_bSn_cLa_dO_{x\pm\delta}$, $La_aCa_bFe_cCo_dO_{x\pm\delta}$, $La_aCa_bMn_cCo_dNi_eAl_fO_{x\pm\delta}$, $Y_aCa_bMn_cO_{x\pm\delta}$, and $Sr_aNa_bSn_cY_dO_{x\pm\delta}$, where a, b, c, d, e and f are each between 0 and 1, the sum of a through f equals 1 to 3, x is the sum of a through f plus 1, and 6 is the vacancy concentration or excess oxygen concentration. While oxygen is indicated in the formulae above, it will be recognized that the positions held by oxygen could be substituted with sulfur.

In yet another embodiment of the present invention, the SHC component is a combination of oxygen and/or sulfur with two or more metals from groups 4-15 of the Periodic Table of the Elements (hereinafter "sub-group 4"). Within sub-group 4, the preferred metals from groups 4-15 are at least two of titanium, zirconium, niobium, molybdenum, tungsten, manganese, iron, cobalt, iridium, nickel, palladium, platinum, copper, zinc, aluminum gallium, indium, germanium, tin, antimony, and bismuth. Even more preferred are titanium, manganese, cobalt, copper, zinc, aluminum, and indium.

Examples of combinations falling within sub-group 4 of the metal combinations are $In_aCu_bMn_cO_{x\pm\delta}$, $Mn_aCo_bO_{x\pm\delta}$, $In_aZn_bMn_cAl_dO_{x\pm\delta}$, $In_aZn_bMn_cO_{x\pm\delta}$, $Mn_aZn_bO_{x\pm\delta}$, $Mn_aZn_bAl_cO_{x\pm\delta}$, $In_aMn_bO_{x\pm\delta}$, $In_aMn_bAl_cO_{x\pm\delta}$, and $Mn_aZn_bTi_cO_{x\pm\delta}$, where a, b, c, and d are each between 0 and 1, the sum of a through d equals 1 to 3, x is the sum of a through d plus 1, and 6 is the vacancy concentration or excess oxygen concentration. While oxygen is indicated in the formulae above, it will be recognized that the positions held by oxygen could be substituted with sulfur.

The remaining component of the SHC component in accordance with the invention is at least one of sulfur and oxygen. Oxygen is preferred. It is noted that at least a portion of the sulfur present in a SHC component could be removed in the SHC reaction and replaced by oxygen in the regeneration process. It is also noted that in embodiments in which the hydrocarbon feed contained sulfur compounds, the SHC component could have sulfur present in the structure. Therefore, it is likely that applications of this invention with sulfur-containing feedstock could involve a SHC component containing both sulfur and oxygen regardless of which is used in the initial formulation of the SHC component.

In a preferred embodiment, the SHC component can adopt a perovskite ($ABO_3$) crystal structure, a spinel ($AB_2O_4$) crystal structure, or a birnessite ($A_zBO_x$) crystal structure, where A and B are two distinct metal sites.

In an embodiment with a perovskite crystal structure, each metal site can comprise one or more metal cations. The crystal structure can be significantly distorted from the idealized cubic, perovskite structure depending on the choice of metals at A and B sites and/or due to the formation of oxygen vacancies upon reduction. In a preferred embodiment, the sum of a through n, in the sample compositions provided above, is 2 and X is 3. The A sites in a perovskite structure are coordinated with 12 oxygen sites. The B sites in the structure would then be occupied by the remaining, generally smaller atoms, and are coordinated with 6 oxygen sites. Selection of A and B metal cations to optimize their relative sizes is desirable for maximum structural stability structure. Different metal cations can be substituted (or doped) at a particular site, and for stability it is desirable that the size of these cations be similar to the size of the cation being replaced. These criteria allow optimization of the selections within each of the desirable combinations of metals from selected groups of the Periodic Table.

Stoichiometric perovskites (e.g., $A^{3+}B^{3+}O^{2-}_3$) have all metal and oxygen sites occupied, whereas non-stoichiometric perovskites (e.g., $A^{3+}_{1-x}A'^{2+}_xB^{3+}O^{2-}_{3-\delta}$) can exist with oxygen vacancies. Oxygen vacancy concentration (6) is governed by charge-neutrality. These oxygen vacancies in the crystal structure provide one mechanism for solid-state diffusion of $O^{2-}$ ions in the crystal lattice. The $O^{2-}$ ions can "jump" or "hop" from occupied sites to vacant sites, and hence diffuse within the lattice. This vacancy hopping mechanism for $O^{2-}$ diffusion has been established in various metal oxide compounds.

The metals are preferably selected to optimize use of oxygen and/or sulfur from the lattice structure as indicated by the relationship below where the presence of reducible metal cations allow oxygen or sulfur to be removed from the lattice:

$$O^{2-} \rightarrow \tfrac{1}{2}O_2 + 2e'+V_O$$

$$M^{n+}+2e' \rightarrow M^{(n-2)+}$$

where $V_O$ denotes an oxygen vacancy formed due to oxygen being removed from the lattice, M is the reducible metal cation, and e is an electron (for a p-type material, holes instead of electrons would be used to denote charge-transfer), where sulfur (S) can be substituted for oxygen (O) throughout. If the metals forming the perovskite or spinel do not reduce, oxygen or sulfur will not be removed from the crystal lattice.

High oxygen diffusivity is necessary to allow $O^{2-}$ ions to diffuse from interior of metal oxide or sulfide particles to the surface where they can react with hydrogen. As stated above, oxygen diffusivity can be increased by creating oxygen vacancies, for example by replacing some of the trivalent La with divalent Ca in the crystal structure of $LaMnO_3$. In addition to oxygen mobility, electronic conductivity is also essential to allow electrons (or holes) to be transported away from (or to) the interface.

For the purposes of this invention, the SHC component will preferably have low reactivity towards hydrocarbons. Combinations of metals may be selected to optimize the properties for a given application. Lower molecular weight materials are generally preferred for the economic benefit of greater oxygen capacity for a given mass of material to be used in the catalyst system.

Preferred crystal structures for the SHC component would demonstrate an ability to sustain oxygen vacancies in crystal structure. Perovskites can accommodate a large vacancy concentration (δ) as large as 0.5 or higher without phase decomposition. This phase stability allows for reversible oxygen and/or sulfur removal from and addition to the SHC component.

Another preferred crystal structure is the spinel ($AB_2O_4$) structure where A and B represent two distinct metal cation sites, where "B" is octahedrally coordinated to 6 oxygen sites and "A" is tetrahedrally coordinated to 4 oxygen sites.

Another preferred structure is the birnessite ($A_zBO_x$) crystal structure, which generally contains layered manganese oxide ($MnO_6^{2-}$) octahedra sheets with "A" cations, typically group 1 or group 2 metal ions, incorporated between $MnO_6$ layers to balance the negative charge on the sheets. Differing amounts of hydration water can also be incorporated between these layers. The birnessite structure can be synthesized along with the spinel structure, and has been observed to transform to a spinel structure. High-temperature stability of birnessite, and its transformation to spinel structure, appears to depend on selection of the stabilizing cation. For example, birnessite structures containing potassium appear to be more stable than those containing sodium.

It is anticipated that other crystalline structures could also be used to provide a SHC component capable of surrendering oxygen to a hydrogen combustion reaction.

The catalyst system of the present invention can also include at least one of at least one support, at least one filler, and at least one binder. The SHC component could be prepared, by way of non-limiting example, by combining salts or chalcogenides (compounds of the group 16 elements) containing the desired parts through such means as evaporation or precipitation, optionally followed by calcination. The aromatization component is then physically mixed or chemically reacted with the SHC component, optionally, combined with a binder to form catalyst particles, and as an additional option, may be combined with a carrier to form slurry.

The SHC component can be obtained through chemical means, such as the combination of metal salts and/or chalcogenides, in solution or slurry, followed by removal of the solvent or mother liquor via evaporation or filtration and drying. Various methods for synthesizing particular compounds are known in the art. The SHC component can then be ground and calcined. The aromatization and SHC components can be physically admixed by mechanical mixing.

The aromatization component and the SHC component of the catalyst system in accordance with the present invention can be chemically bound. The chemically bound materials can then be subjected to the treatment of a matrix component. The matrix component serves several purposes. It can bind the aromatization component and the SHC component to form catalyst particles. It can serve as a diffusion medium for the transport of feed and product molecules. It can also act as a filler to moderate the catalyst activity. In addition, the matrix can help heat transfer or serve as a sink or trap for metal contaminants in the feedstock.

Examples of typical matrix materials include amorphous compounds such as silica, alumina, silica-alumina, silica-magnesia, titania, zirconia, and mixtures thereof. It is also preferred that separate alumina phases be incorporated into the inorganic oxide matrix. Species of aluminum oxyhydroxides-γ-alumina, boehmite, diaspore, and transitional aluminas such as α-alumina, β-alumina, γ-alumina, δ-alumina, ε-alumina, κ-alumina, and ρ-alumina can be employed. Preferably, the alumina species is an aluminum trihydroxide such as gibbsite, bayerite, nordstrandite, or doyelite. The matrix material may also contain phosphorous or aluminum phosphate. The matrix material may also contain clays such as halloysite, kaolinite, bentonite, attapulgite, montmorillonite, clarit, fuller's earth, diatomaceous earth, and mixtures thereof. The weight ratio of the aromatization component and the SHC component to the inorganic oxide matrix component can be about 100:1 to 1:100.

In another aspect of the present invention, the aromatization component and the SHC component may be treated separately with a matrix component. The matrix component for the aromatization component can be the same as or different from that for the SHC component. One of the purposes of the treatment is to form particles of the aromatization component and particles of the SHC component so that the components are hard enough to survive inter-particle and reactor wall collisions. The matrix component may be made according to conventional methods from an inorganic oxide sol or gel, which is dried to "glue" the catalyst particle's components together. The matrix component can be catalytically inactive and comprises oxides of silicon, aluminum, and mixtures thereof. It is also preferred that separate alumina phases be incorporated into the inorganic oxide matrix. Species of aluminum oxyhydroxides-γ-alumina, boehmite, diaspore, and transitional aluminas such as α-alumina, β-alumina, γ-alumina, δ-alumina, ε-alumina, κ-alumina, and ρ-alumina can be employed. Preferably, the alumina species is an aluminum trihydroxide such as gibbsite, bayerite, nordstrandite, or doyelite. The matrix material may also contain phosphorous or aluminum phosphate. The matrix material may also contain clays such as kaolinite, bentonite, attapulgite, montmorillonite, clarit, fuller's earth, diatomaceous earth, and mixture thereof.

The weight ratio of the aromatization component to the matrix component can be about 100:1 to 1:100. The weight ratio of the SHC component to the matrix component can be about 100:1 to 1:100.

In accordance with the present invention, the weight ratio of aromatization component to the total weight of SHC component is from 1000:1 to 1:1000. More preferably, the ratio is from 500:1 to 1:500. Most preferably, the ratio is from 100:1 to 1:100. This ratio can be adjusted and optimized for a given feedstock and desired product slate.

The aromatization component particles and the SHC component particles may be mixed to form a uniform catalyst system in the reactor or be packed in series to form a staged catalyst system in either a single reactor or two or more staged reactors. Preferably, the catalyst system components are mixed to form a uniform catalyst system.

Non-limiting Illustrative Processes

An aspect of the invention relates to a hydrocarbon conversion process using the inventive catalyst system in any known reactor suitable for aromatization reactions and selective hydrogen combustion reactions. By way of non-limiting, illustrative example, fixed-bed reactors with catalyst regeneration, moving bed reactors with catalyst regeneration such as the continuous catalyst regeneration reactor (also known as CCR), fluidized-bed processes such as a riser reactor with catalyst regeneration and the like would be suitable. Examples of fixed-bed catalytic reactors include fixed-bed tubular reactors. A non-limiting illustrative example of a suitable fixed-bed catalyst regeneration system is illustrated in U.S. Pat. No. 5,059,738 to Beech, Jr. et al, which is incorporated herein by reference in its entirety. A non-limiting illustrative example of a suitable continuous catalyst regeneration moving bed reactor is illustrated in U.S. Pat. No. 5,935,415 to Haizmann et al, which is incorporated herein by reference in its entirety.

The overall hydrocarbon conversion processes, i.e., the simultaneous (i) aromatization reactions and (ii) selective hydrogen combustion reactions are carried out in the presence of catalyst systems, and are believed to be catalytic processes. The conversion reactions can be carried out at temperatures and pressures effective for converting oxygenated hydrocarbon to aromatics. For example, the hydrocarbon conversion processes are particularly efficient when carried out at reaction zone temperatures of from 300° C. to 800° C. Alternatively, the overall hydrocarbon conversion process to produce the aromatics is particularly efficient at reaction zone temperatures of from 300° C. to 600° C., or at temperatures of from 300° C. to 550° C.

The inventive catalyst system must be regenerated with an oxidant to replenish the lattice oxygen of the SHC component of the catalyst system and to remove at least a portion of any coke on the catalyst system components. Regeneration temperatures can be in the range of about 300 to about 800° C.

Operating pressures may include a pressure of at least atmospheric pressure (zero pressure, gauge), such as ≥4 pounds per square inch gauge (psig) (28 kilo Pascals gauge (kPag)), or ≥15 psig (103 kPag), or ≥36 psig (248 kPag), or ≥44 psig (303 kPag), or ≥103 psig (709 kPag), but may be ≤300 psig (2064 kPag), or ≤163 psig (1121 kPag), or ≤150 psig (1032 kPag).

Also, as may be appreciated, these different pressures and temperatures may be utilized together to form different combinations depending on the specific configuration of equipment.

A flow-through reactor that would be suitable for use in practicing the inventive process is disclosed in U.S. patent application Ser. No. 14/469,141, filed Aug. 26, 2014, which is incorporated herein by reference in its entirety.

In certain aspects, the invention relates to a reaction system that includes a reactor comprising: (i) a first region having a first aperture; (ii) a second region having a second aperture; and (iii) a catalytic conversion zone containing a catalyst system comprising (1) at least one aromatization component and (2) at least one selective hydrogen combustion ("SHC") component. The first and second regions can be configured for flowing an oxidant to enter the reactor proximate to the first aperture at a first time interval, and for flowing an oxygenated hydrocarbon feed to enter the reactor proximate to the first aperture at a second time interval, with the first and second time intervals being at separate time intervals relative to one another. The first and second regions can be further configured to flow one or more components of a reaction mixture to exit the reactor proximate to the second aperture.

Optionally, the reactor of the reaction system can be a reverse-flow reactor. For example, the reverse-flow reactor can be configured for flowing an oxidant to enter the reactor proximate to the first aperture at a first time interval (forward direction), and a second flow of an oxygenated hydrocarbon feed to enter the reactor proximate to the second aperture at a second time interval (reverse direction). The reactor can be further configured to exit one or more components of a reaction mixture proximate to the first aperture.

Flow-through type reactors are particularly suitable for carrying out the simultaneous aromatization reactions and selective hydrogen combustion reactions in the presence of the specified catalyst system. As a first step, or during a first time interval, oxidant is passed through the flow-through reactor. The flow-through reactor is maintained under conditions of temperature, pressure, and flow sufficient to regenerate the components of the catalyst system including (i) transferring oxygen from the oxidant to the selective hydrogen combustion ("SHC") component, (ii) storing the transferred oxygen within the SHC component lattice, and (iii) removing by oxidation or combustion any coke deposits from both the SHC and aromatization components of the catalyst system.

Optionally, when additional heat is needed, this can be provided to the flow-through reactor by one or more of (i) heating the oxidant upstream of or in the flow-through reactor, and (ii) introducing a hydrocarbon fuel with the oxidant to combust and exothermically release heat to the flow-through reactor. When the oxidant provides heat to the flow-through reactor, the oxidant can be referred to as "heating fluid". Heating fluid can be utilized, e.g., when the overall hydrocarbon conversion process, namely the simultaneous aromatization reactions and selective hydrogen combustion reactions, is net endothermic.

When the overall hydrocarbon conversion process is net exothermic, heat is removed to maintain the specified conversion conditions. Heat may be removed via any known method including but not limited to (i) cooling the oxygenated hydrocarbon feed before it is introduced to the reactor or (ii) cooling the reactor via indirect heat transfer with a cooling medium.

During the first time interval, oxygen is transferred from the oxidant to the SHC component. Additionally, sufficient oxygen and/or heat is passed through the reactor to remove from both the aromatization component and the SHC component of the catalyst system any coke by oxidation or combustion. Oxidant flow is lessened or stopped after (i) sufficient oxygen is stored with the SHC catalyst for carrying out the selective hydrogen combustion (ii) sufficient heat is added (if any is needed) for carrying out the hydrocarbon conversion process, and (iii) sufficient coke is removed.

During a subsequent or second time interval, oxygenated hydrocarbon feed is passed through the flow-through reactor under conditions of pressure, temperature and flow sufficient for aromatizing at least a portion of the oxygenated hydrocarbon feed. As the oxygenated hydrocarbon feed flows through the reactor, at least a portion of the oxygenated hydrocarbon feed is aromatized producing aromatics and hydrogen, among other products, in the presence of at least the aromatization component of the catalyst system. Simultaneously, at least a portion of the produced hydrogen reacts with the stored oxygen in the SHC component of the catalyst system to form water.

The aromatization of the oxygenated hydrocarbon feed in the presence of the aromatization component of the catalyst system and the combustion of the produced hydrogen with the SHC stored oxygen oxidant in the presence of the SHC component of the catalyst system produces a reaction mixture comprising (i) aromatics and (ii) water.

Oxidant and oxygenated hydrocarbon feed can be flowed in the same direction in the flow-through reactor ("uniflow"), provided each flow is carried out during separate time intervals. For example, during a first time interval an oxidant can be flowed in a forward direction. During a second or subsequent time interval, the oxygenated hydrocarbon feed can be flowed in the forward direction through the flow-through reactor.

If desired, a sweep fluid can be passed through the flow-through reactor during a time interval between the first time interval and the second time interval. The sweep fluid can be passed in the forward direction or the reverse direction. Typical sweep fluids include relatively inert liquids and vapors, especially those which are relatively easy to separate from the aromatics products. Steam and/or molecular nitrogen are examples of suitable sweep fluids.

Reverse-flow catalytic reactors can be used to carry out the catalytic hydrocarbon conversions, including one or more conventional reverse-flow reactors. Reactors typically used for converting reactions, and to execute cyclic, high temperature chemistry, can be used, such as those described in U.S. Pat. Nos. 7,943,808, 7,491,250, 7,846,401, and 7,815,873.

Generally, forward and reverse flows through reverse-flow catalytic reactors are carried out during separate time intervals. For example, oxidant can be flowed in a first or forward direction through the reverse-flow reactor, during a first time interval. During a second or subsequent time interval, oxygenated hydrocarbon feed can be flowed in a second or reverse direction through the reverse-flow reactor.

Regenerative, reverse-flow catalytic reactors can be used to carry out (i) the aromatization reactions and (ii) the selective hydrogen combustion reactions. A regenerative, reverse-flow reactor is (i) "reverse flow" in the sense that an upstream region of the reactor with respect to the average flow of the first feed mixture corresponds to the downstream region with respect to the average flow of the second feed mixture and (ii) "regenerative" in the sense that at least a portion of any heat lost during a time interval is restored by heat released during a subsequent interval (and vice versa). Regenerative, reverse-flow reactors may be particularly advantageous when the overall hydrocarbon conversion process is net endothermic.

A variety of flow-through reactors are suitable. The flow-through reactor can be physically symmetric, e.g., a reverse-flow reactor that is symmetric about a central axis. The flow-through reactor can be adiabatic, e.g., an adiabatic reverse-flow reactor. The flow-through reactor can include a housing, a plurality of flow-control means (e.g., conduits and valves), one or more insulation components (e.g., insulation bricks) and one or more process flow components (e.g., thermal mass, mixing components, etc.). The housing may be utilized to enclose an interior region and has one or more insulation components disposed adjacent to the housing. The plurality of flow control means may include one or more conduits, one or more apertures, and one or more valves that are configured to manage the flow of one or more streams into and out of the interior region from a location external to the interior region or housing. Process flow components can be configured and/or arranged to manage the flow of fluids through the interior region.

Regenerative reverse-flow reactors may involve multiple steps repeated in sequence to form a cycle for the process. For example, the process can include two or more sequential steps, such as two or more steps operated continuously in sequence (one step after the other). The steps can include, e.g., (i) a net endothermic, forward-flow oxygen transfer/storage and reactor regeneration step, (ii) a net exothermic, reverse-flow, hydrocarbon conversion step, (iii) a repetition of the forward-flow oxygen transfer/storage and reactor regeneration step, and (iv) a repetition of the reverse-flow hydrocarbon conversion step. As part of these steps, valves may be utilized to alternate introduction of feed mixtures into the reactor, e.g., a first feed mixture comprising oxidant and a second feed mixture comprising oxygenated hydrocarbon feed.

A first feed stream to the flow-through reactor includes oxidant (optionally as a heating fluid or a component thereof), which can be passed to the flow-through reactor at a first time interval. A second feed stream to the flow-through reactor includes oxygenated hydrocarbon, which can be passed to the flow-through reactor at a second time interval.

Using continuous catalyst regeneration technology would also overcome the potential problem related to lattice oxygen being quickly consumed with resultant loss of catalyst activity. A fluidized bed reactor-regenerator system is a suitable continuous catalyst regeneration technology for carrying out the hydrocarbon conversion process. A non-limiting example of such a reactor system is a downer-regenerator or a riser-regenerator system as described below for illustration purposes only. A riser-regenerator system that would be suitable for use in practicing the inventive process is disclosed in U.S. Pat. No. 5,002,653, which is incorporated herein by reference in its entirety.

In a riser-regenerator system, oxygenated hydrocarbon feed is contacted with the inventive catalyst system in a feed riser line (a reaction zone) wherein the simultaneous aromatization and selective hydrogen combustion conversion reactions primarily take place. The catalyst to oxygenated hydrocarbon feed ratio, weight basis, can be in the range of 0.01 to 1000. The residence time in the reaction zone can be in the range of 0.01 second to 10 hours. Though not required, it is preferred that the feed's residence time in the reaction zone be less than about 100 seconds, for example from about 0.01 to about 60 seconds, preferably from about 0.1 to about 30 seconds.

As the conversion reactions progress, the catalyst system is progressively deactivated primarily by consumption of lattice oxygen from the SHC component but also by the formation of coke on all components of the catalyst system surface. The catalyst system and conversion products are separated mechanically and any hydrocarbons remaining on the catalyst are removed by steam stripping before the catalyst system enters a catalyst regenerator. The conversion products are taken overhead to a series of fractionation towers for product separation. The at least partially deactivated catalyst system is reactivated in the regenerator by introducing an oxidant, such as air, to replenish the catalyst system's lattice oxygen consumed in the reactor. The introduction of oxidant also burns off any coke deposits on the catalyst system. As required, a small amount of fresh make-up catalyst system can be added to the reactor or, preferably, to the regenerator.

The hydrocarbon conversion process of the present invention may also be performed in one or more conventional FCC process units in the presence of the catalyst system of this invention. Each unit comprises a riser reactor having a reaction zone, a stripping zone, a catalyst regeneration zone, and at least one fractionation zone. The oxygenated hydrocarbon feed is conducted to the riser reactor where it is injected into the reaction zone wherein the feed contacts a flowing source regenerated catalyst. The catalyst aromatizes the feed and selectively combusts the resultant hydrogen. The aromatization reaction may deposit carbonaceous hydrocarbons, or coke, on the catalyst system and the selective hydrogen combustion reaction depletes the lattice oxygen of the SHC component, thereby at least partially deactivating the catalyst system. The conversion products may be separated from the partially deactivated catalyst system and a portion of the conversion products may be fed to a fractionator. The fractionator generally separates at least a fraction comprising aromatics from the conversion products.

The deactivated catalyst system flows through the stripping zone where volatile hydrocarbons are stripped from the catalyst particles with a stripping material such as steam. The stripped catalyst is then conducted to the regeneration zone where it is regenerated by burning any coke on the catalyst system and replenishing the oxygen-depleted SHC catalyst component in the presence of an oxidant, preferably air. Decoking and oxidation restore catalyst activity. The catalyst is then recycled to the riser reactor at a point near or just upstream of the reaction zone. Flue gas formed by burning coke in the regenerator may be treated for removal of particulates and for conversion of carbon monoxide, after which the flue gas is normally discharged into the atmosphere.

The overall hydrocarbon conversion may be net exothermic or net endothermic. When the hydrocarbon conversion is net endothermic, the stripping may be performed under low severity conditions in order to retain absorbed hydrocarbons for heat balance through combustion in the regenerator. The heat from combustion is transferred to the catalyst system and heated catalyst is carried to the reaction zone. Alternatively, when the hydrocarbon conversion is net exothermic, heat may be removed by any conventional method. A suitable method of heat removal is the addition of catalyst coolers to the reactor system. A non-limiting example of catalyst coolers is described in U.S. Pat. No. 4,328,384 which is incorporated here by reference in its entirety. A slip stream of catalyst is withdrawn from the fluidized reactor system. The catalyst is indirectly cooled by a cooling medium, such as water, as the catalyst passes downward through the catalyst cooler. Stripping gas, such as steam, is introduced counter-current to the catalyst flow and strips volatile hydrocarbons from the catalyst. The stripping gas and volatile hydrocarbons exit the top of the catalyst cooler and are reintroduced to the reactor system. Cooled catalyst exits the bottom of the catalyst cooler and is reintroduced into the fluidized reactor system, for example, at the riser reaction zone. Catalyst coolers could be added to the riser reactor, regenerator, or both.

EXAMPLES

The invention is illustrated in the following non-limiting examples, which are provided for the purpose of representation, and are not to be construed as limiting the scope of the invention. All parts and percentages in the examples are by weight unless indicated otherwise.

Example 1

Certain embodiments of the invention are depicted in FIG. 1. FIG. 1 illustrates a flow-through reactor, for example a catalytic reverse-flow reactor having a first region 1 and a second region 2. The reaction zone 3 contains the catalyst system, comprising at least one SHC component and at least one aromatization component. The invention, however, is not limited to catalytic reverse-flow reactors having two regions.

An example of the hydrocarbon conversion process for producing an aromatics composition can be described with reference to FIG. 1. During a first step of the process for producing the aromatics composition, or during a first time interval, oxidant is passed through the flow-through reactor in a forward direction, as shown by the direction of the arrow. Oxygen from the oxidant is stored with the SHC component of the catalyst system in reaction zone 3 as the oxidant is passed through the reactor. At least a portion of any coke on or in the reactor or the catalyst system is removed via combustion or oxidation with the oxygen from the oxidant. Over a desired cycle time, the flow of the heating fluid is stopped.

During a second time interval, a feed containing ≥10.0 wt. % oxygenated hydrocarbon (e.g., methanol), based on total weight of the feedstream, is passed through the flow-through reactor. The feed passes across or through reaction zone 3, with at least a portion of the oxygenated hydrocarbon in the feed being aromatized in the presence of the aromatization component of the catalyst system to produce aromatics and hydrogen, among other products. Simultaneously, the produced hydrogen is selectively combusted or oxidized in the presence of oxygen stored in the SHC component of the catalyst system. This results in a conversion mixture comprising an aromatics product composition. The conversion mixture can be conducted away from the reactor for further processing, such as separation of aromatics from other conversion products.

The oxidant and oxygenated hydrocarbon feed can be flowed in the same direction (i.e., a forward direction as shown by the arrow of FIG. 1) as long as the flows are at separate time intervals. For example, the oxidant can be flowed in a forward direction through the flow-through reactor, during a first time interval. During a second or subsequent time interval, the hydrocarbon reactant also can be flowed in the forward direction through the flow-through reactor.

The flow-through reactor of FIG. 1 can be operated as a reverse-flow reactor, with the oxidant/regeneration step being carried out in a first time interval and the hydrocarbon conversion step being carried out in a second time interval. When the process is carried out in a reverse-flow arrangement, oxidant and oxygenated hydrocarbon feed are flowed in opposite directions through the reverse-flow reactor at separate time intervals.

As shown in FIG. 1, the heating fluid is flowed in a first or forward direction through the flow-through reactor, during a first time interval. When the flow-through reactor is operated in a reverse-flow arrangement, during a second or subsequent time interval, the oxygenated hydrocarbon feed is flowed in a second or reverse direction of the arrow shown in FIG. 1.

The first and second time intervals, as generally described according to the exemplary scheme shown in FIG. 1, can be substantially non-overlapping intervals. Each of the first and second time intervals can be, independently, an interval having a duration in the range of from about 0.5 seconds to about 15 seconds. The interval between the first and second time intervals (the "dead-time", which represents the interval of time it takes to reverse flow of the feed mixtures) is preferably as short as possible so that the reverse flow cycle can be as rapid as possible. From a practical standpoint, the dead-time should be, e.g., ≤ than 0.5 seconds, such as in a range of from about 0.01 seconds to about 0.5 seconds. Upon completion of the second time interval, the intervals can be repeated. That is, the flow shown in FIG. 1 can be reinitiated and followed by subsequent re-initiation of the flow shown in FIG. 1.

In the exemplary embodiment shown in FIG. 1, the oxidant can comprise ≥90.0 wt. % of $O_2$, e.g., $O_2$ obtained from air, based on total weight of the oxidant. The oxygenated hydrocarbon feed can comprise ≥80 wt. % methanol.

What is claimed is:

1. A hydrocarbon conversion process, comprising:
   (a) providing a flow-through reactor system containing a catalyst system comprising
      (i) at least one aromatization component comprising a molecular sieve and (ii) at least one selective hydrogen combustion component comprising a mixed metal oxide or a mixed metal sulfide, wherein the selective hydrogen combustion component comprises at least one metal from Groups 2, 3, or 7, at least one metal from Groups 11-15 of the Periodic Table of Elements, and at least one oxygen or sulfur, and wherein the at least one of oxygen or sulfur is chemically bound both within and between the at least one metal from Groups 2, 3, or 7 and the at least one metal from Groups 11-15 of the Periodic Table of Elements;
   (b) during a first time interval,
      i. passing a free-oxygen containing gas through the flow-through reactor system,
      ii. transferring at least a portion of the free-oxygen containing gas's oxygen to the selective hydrogen combustion component for storage,
      iii. removing at least a portion of any coke from the catalyst system by oxidation or combustion with the free-oxygen containing gas oxygen, and
      v. lessening or discontinuing the passing of the free-oxygen containing gas through the flow-through reactor system;
   (c) during a second time interval,
      i. passing an oxygenated hydrocarbon feed through the flow-through reactor system, wherein the oxygenated hydrocarbon feed includes one or more of aliphatic aldehydes, carboxylic acids, carbohydrates, alcohols, ethers, and acetals,
      ii. converting at least a portion of the oxygenated hydrocarbon feed to aromatics and hydrogen in the presence of at least the aromatization component of the catalyst system,
      iii. selectively combusting at least a portion of the hydrogen with stored oxygen in the selective hydrogen combustion component of the catalyst system to form water without substantially combusting any of the aromatics or any of the oxygenated hydrocarbon feed; and
   (d) conducting at least a portion of a conversion products mixture comprising aromatics and water away from the flow-through reactor system.

2. The process of claim 1, wherein the selective hydrogen combustion is accomplished without a feeding of free-oxygen containing gas into the reactor.

3. The process of claim 1, wherein the feed comprises methanol and the process is conducted at a temperature from about 300° C. to about 800° C. and a pressure from 1 to 20 atmospheres absolute (101 to 2064 kPa).

4. The process of claim 1, further comprising the step of removing heat from the process where the removed heat is less than 90% of the removed heat required in a hydrocarbon conversion process for converting an oxygenate hydrocarbon feed to aromatics operated under the same conditions without a selective hydrogen combustion component in the catalyst system.

5. The process of claim 1, wherein added heat is required to maintain a steady conversion temperature.

6. The process of claim 1, wherein a yield of hydrogen is at least 10% less than the yield of hydrogen when converting said oxygenated hydrocarbon feed(s) under the same conditions without a selective hydrogen combustion component in the catalyst system.

7. The process of claim 1, wherein the at least one metal from Groups 11-15 of the Periodic Table of Elements is selected from the list consisting of copper, zinc, aluminum, gallium, germanium, silver, tin, antimony, and bismuth.

8. A hydrocarbon conversion process comprising:
   (A) charging at least one oxygenated hydrocarbon feed to a fluidized bed reactor, wherein the oxygenated hydrocarbon feed includes one or more of aliphatic aldehydes, carboxylic acids, carbohydrates, alcohols, ethers, and acetals,
   (B) charging a fluidized catalyst system from a catalyst regenerator to the fluidized bed reactor, said catalyst system comprising (1) at least one aromatization component comprising a molecular sieve and (2) at least one selective hydrogen combustion component comprising a mixed metal oxide or a mixed metal sulfide wherein the selective hydrogen combustion component comprises at least one metal from Groups 2, 3, or 7, at least one metal from Groups 11-15 of the Periodic Table of Elements, and at least one of oxygen or sulfur, wherein the at least one of oxygen or sulfur is chemically bound both within and between the at least one metal from Groups 2, 3, or 7 and the at least one metal from Groups 11-15 of the Periodic Table of Elements,
   (C) catalytically converting the oxygenated hydrocarbon feed to aromatics and selectively combusting resultant hydrogen in the presence of the catalyst system to produce a stream of conversion products, comprising aromatics and water, and an at least partially deactivated catalyst system which are discharged from the fluidized bed reactor,
   (D) separating a phase rich in the conversion products from a phase rich in the deactivated catalyst system,
   (E) stripping any retained volatile conversion products off the deactivated catalyst system with a stripping material at stripping conditions to produce a stripped catalyst system phase,
   (F) reactivating the stripped catalyst phase with a free-oxygen containing gas in the catalyst regenerator at regeneration conditions to produce the fluidized catalyst system, which is recycled to the fluidized bed reactor, and
   (G) separating and recovering the conversion products.

9. The process of claim 8, wherein the feed comprises methanol and the process is conducted at a temperature from about 300° C. to about 800° C. and a pressure from 1 to 20 atmospheres absolute (101 to 2064 kPa).

10. The process of claim 8, wherein the at least one metal from Groups 11-15 of the Periodic Table of Elements is selected from the list consisting of copper, zinc, aluminum, gallium, germanium, silver, tin, antimony, and bismuth.

* * * * *